(12) United States Patent
Nam et al.

(10) Patent No.: US 9,862,668 B2
(45) Date of Patent: Jan. 9, 2018

(54) MONOMER, POLYMER, ORGANIC LAYER COMPOSITION, ORGANIC LAYER, AND METHOD OF FORMING PATTERNS

(71) Applicant: SAMSUNG SDI CO., LTD., Yongin-si, Gyeonggi-do (KR)

(72) Inventors: Youn-Hee Nam, Suwon-si (KR); Hyo-Young Kwon, Suwon-si (KR); Sung-Hwan Kim, Suwon-si (KR); Seung-Hyun Kim, Suwon-si (KR); Ran Namgung, Suwon-si (KR); Dominea Rathwell, Suwon-si (KR); Soo-Hyoun Mun, Suwon-si (KR); Seulgi Jeong, Suwon-si (KR); Hyeon-Il Jung, Suwon-si (KR); Yu-Mi Heo, Suwon-si (KR)

(73) Assignee: SAMSUNG SDI CO., LTD., Yongin-Si, Gyeonggi-Do (KR)

( * ) Notice: Subject to any disclaimer, the term of this patent is extended or adjusted under 35 U.S.C. 154(b) by 0 days.

(21) Appl. No.: 14/886,121

(22) Filed: Oct. 19, 2015

(65) Prior Publication Data
US 2016/0145379 A1  May 26, 2016

(30) Foreign Application Priority Data

Nov. 24, 2014 (KR) .......................... 10-2014-0164607
Jul. 31, 2015 (KR) .......................... 10-2015-0109027

(51) Int. Cl.
| | | |
|---|---|---|
| C08G 61/10 | (2006.01) | |
| C07C 43/23 | (2006.01) | |
| C08G 61/02 | (2006.01) | |
| C09D 165/00 | (2006.01) | |

(52) U.S. Cl.
CPC .............. *C07C 43/23* (2013.01); *C08G 61/02* (2013.01); *C09D 165/00* (2013.01); *C07C 2603/50* (2017.05); *C07C 2603/52* (2017.05); *C08G 2261/1422* (2013.01); *C08G 2261/1424* (2013.01); *C08G 2261/312* (2013.01); *C08G 2261/314* (2013.01); *C08G 2261/3424* (2013.01); *C08G 2261/362* (2013.01); *C08G 2261/45* (2013.01); *C08G 2261/72* (2013.01)

(58) Field of Classification Search
None
See application file for complete search history.

(56) References Cited

U.S. PATENT DOCUMENTS

2015/0338423 A1* 11/2015 Shetty .................... C08G 64/20
436/501

FOREIGN PATENT DOCUMENTS

| CN | 102540729 A | 7/2012 | |
|---|---|---|---|
| CN | 103910610 A | 7/2014 | |
| JP | 4355643 B2 | 11/2009 | |
| JP | 4388429 B2 | 12/2009 | |
| JP | 5382390 B2 | 1/2014 | |
| JP | 2014-029435 A | 2/2014 | |
| KR | 10-2013-0026912 A | 3/2013 | |
| KR | 10-2014-0052441 A | 5/2014 | |
| KR | 10-2014-0083695 A | 7/2014 | |
| KR | 10-1413071 B1 | 7/2014 | |
| TW | 201425292 A | 7/2014 | |
| TW | 201425359 | * 7/2014 | ............ C08F 291/00 |
| TW | 201425359 A | 7/2014 | |
| TW | 201425452 A | 7/2014 | |
| TW | 201426196 A | 7/2014 | |
| TW | 201426198 | * 7/2014 | ................ G03F 7/11 |
| TW | 201426198 A | 7/2014 | |
| WO | WO 2013/018802 A1 | 2/2013 | |
| WO | WO2014080977 A1 | * 5/2014 | ............. C08L 63/00 |

OTHER PUBLICATIONS

Taiwanese Search Report dated Aug. 23, 2016 in Corresponding Taiwanese Patent Application No. 104135514.
Klokkenburg, et al., Electron Delocalization in Cross-Conjugated p-Phenylenevinylidene Oligomers. Chem. Eur. J. 2003. 9, pp. 3544-3554. Wiley-VCH Verlag GmbH.
Chinese Office Action/Search Report dated Jul. 3, 2017, of the corresponding Chinese Patent Application No. 201510725055.3.

* cited by examiner

*Primary Examiner* — Rosalynd A Keys
(74) *Attorney, Agent, or Firm* — Lee & Morse, P.C.

(57) ABSTRACT

A monomer, a polymer, an organic layer composition, an organic layer and associated methods, the monomer being represented by Chemical Formula 1:

[Chemical Formula 1]

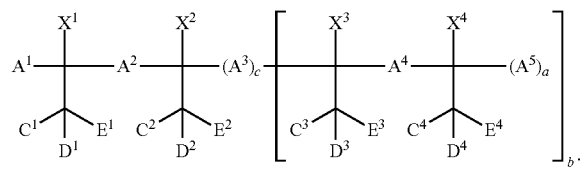

22 Claims, No Drawings

MONOMER, POLYMER, ORGANIC LAYER COMPOSITION, ORGANIC LAYER, AND METHOD OF FORMING PATTERNS

CROSS-REFERENCE TO RELATED APPLICATION

Korean Patent Application Nos. 10-2014-0164607, filed on Nov. 24, 2014, and 10-2015-0109027, filed on Jul. 31, 2015, in the Korean Intellectual Property Office, and entitled: "Monomer, Polymer, Organic Layer Composition, Organic Layer, and Method of Forming Patterns," is incorporated by reference herein in its entirety.

BACKGROUND

1. Field

Embodiments relate to a monomer, polymer, organic layer composition, and a method of forming patterns.

2. Description of the Related Art

Recently, an ultra-fine technique having a pattern of several to several tens nanometer size has been considered. Such ultrafine techniques utilize effective lithographic techniques. Some lithographic techniques may include providing a material layer on a semiconductor substrate; coating a photoresist layer thereon; exposing and developing the same to provide a photoresist pattern; and etching the material layer using the photoresist pattern as a mask.

SUMMARY

Embodiments are directed to a monomer, polymer, organic layer composition, and a method of forming patterns.

The embodiments may be realized by providing a monomer represented by Chemical Formula 1:

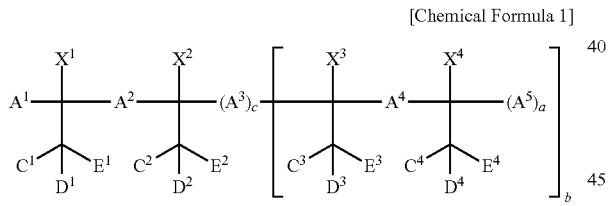

[Chemical Formula 1]

wherein, in Chemical Formula 1, $A^1$, $A^2$, $A^3$, $A^4$, and $A^5$ are each independently a substituted or unsubstituted aromatic ring group, $X^1$, $X^2$, $X^3$, and $X^4$ are each independently a hydroxy group, a substituted or unsubstituted amino group, a halogen atom, a substituted or unsubstituted C1 to C30 alkyl group, a substituted or unsubstituted C6 to C30 aryl group, a substituted or unsubstituted C1 to C30 alkoxy group, a substituted or unsubstituted C3 to C30 cycloalkenyl group, a substituted or unsubstituted C1 to C20 alkylamine group, a substituted or unsubstituted C7 to C20 arylalkyl group, a substituted or unsubstituted C1 to C20 heteroalkyl group, a substituted or unsubstituted C2 to C30 heterocycloalkyl group, a substituted or unsubstituted C2 to C30 heteroaryl group, a substituted or unsubstituted C1 to C4 alkyl ether group, a substituted or unsubstituted C7 to C20 arylalkylene ether group, a substituted or unsubstituted C1 to C30 haloalkyl group, or a combination thereof, $C^1$, $C^2$, $C^3$, $C^4$, $D^1$, $D^2$, $D^3$, $D^4$, $E^1$, $E^2$, $E^3$, and $E^4$ are each independently hydrogen atom, hydroxy group, a substituted or unsubstituted amino group, a halogen atom, a substituted or unsubstituted C1 to C30 alkyl group, a substituted or unsubstituted C6 to C30 aryl group, a substituted or unsubstituted C1 to C30 alkoxy group, a substituted or unsubstituted C3 to C30 cycloalkenyl group, a substituted or unsubstituted C1 to C20 alkylamine group, a substituted or unsubstituted C7 to C20 arylalkyl group, a substituted or unsubstituted C to C20 heteroalkyl group, a substituted or unsubstituted C2 to C30 heterocycloalkyl group, a substituted or unsubstituted C2 to C30 heteroaryl group, a substituted or unsubstituted C1 to C4 alkyl ether group, a substituted or unsubstituted C7 to C20 arylalkylene ether group, a substituted or unsubstituted C1 to C30 haloalkyl group, or a combination thereof, and a, b, and c are each independently 0 or 1.

$A^1$, $A^2$, $A^3$, $A^4$ and $A^5$ may each independently be a substituted or unsubstituted aromatic ring group below:

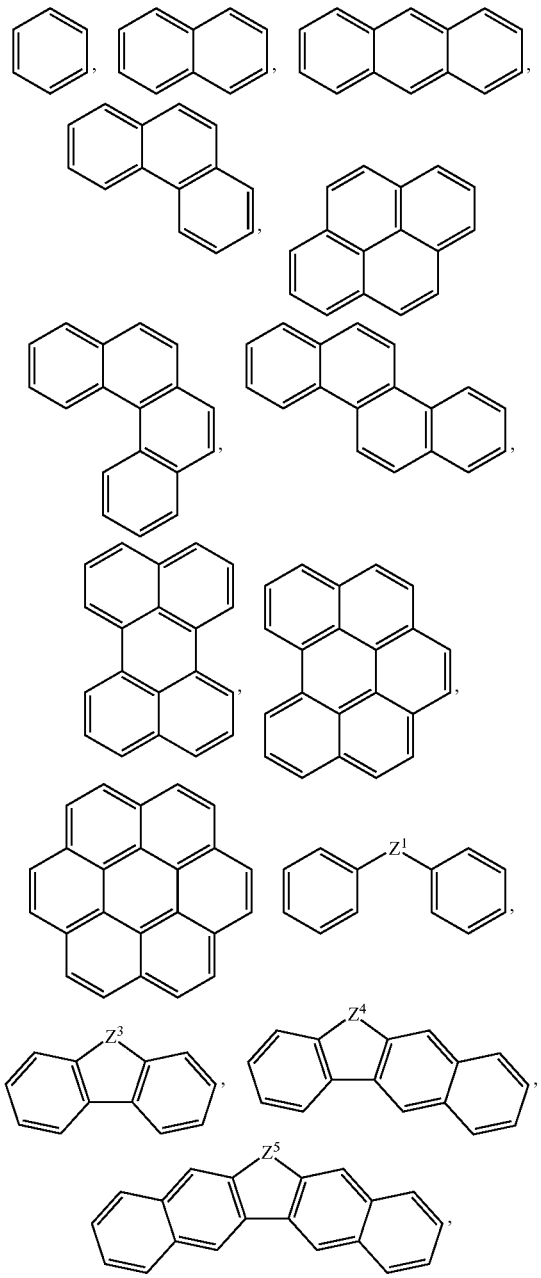

-continued

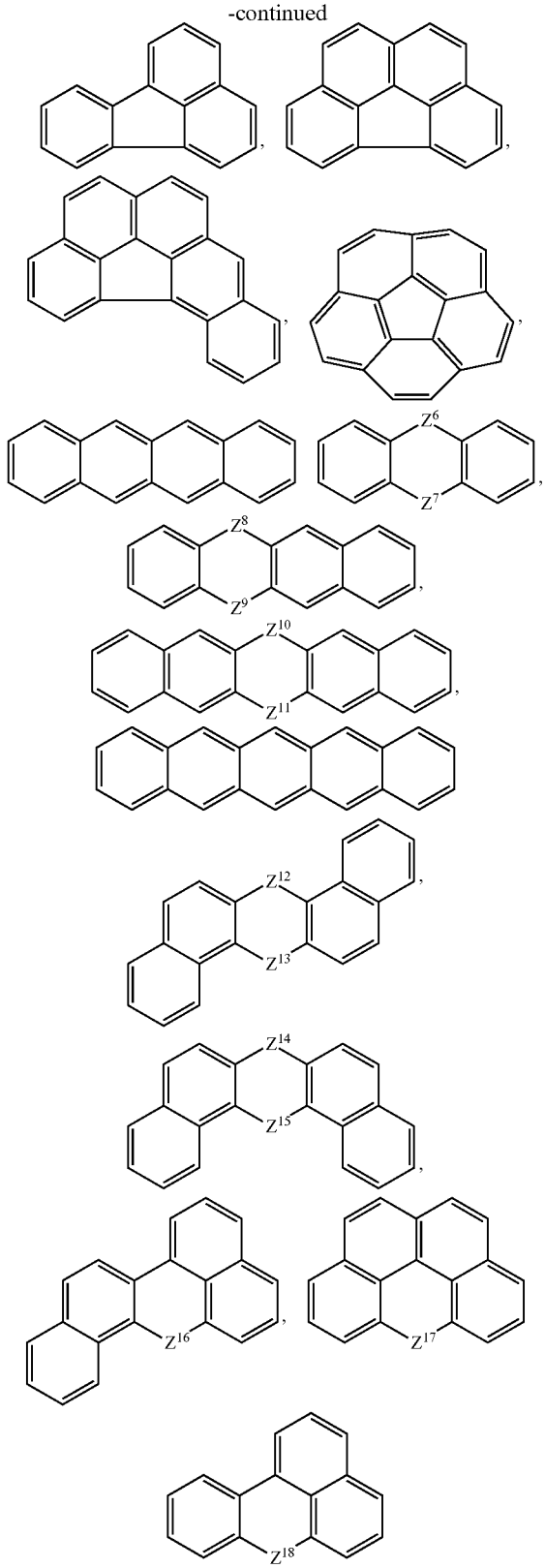

wherein, in the groups above, $Z^1$ may be a single bond, a substituted or unsubstituted C1 to C20 alkylene group, a substituted or unsubstituted C3 to C20 cycloalkylene group, a substituted or unsubstituted C6 to C20 arylene group, a substituted or unsubstituted C2 to C20 heteroarylene group, a substituted or unsubstituted C2 to C20 alkenylene group, a substituted or unsubstituted C2 to C20 alkynylene group, C=O, $NR^a$, oxygen (O), sulfur (S), or a combination thereof, wherein $R^a$ is hydrogen, a substituted or unsubstituted C1 to C10 alkyl group, a substituted or unsubstituted C6 to C20 arylene group, a substituted or unsubstituted C2 to C20 heteroarylene group, a halogen atom, or a combination thereof, $Z^3$ to $Z^{18}$ may each independently be C=O, $NR^a$, oxygen (O), sulfur (S), $CR^bR^c$, or a combination thereof, in which $R^a$ to $R^c$ are each independently hydrogen, a substituted or unsubstituted C1 to C10 alkyl group, a substituted or unsubstituted C6 to C20 arylene group, a substituted or unsubstituted C2 to C20 heteroarylene group, a halogen atom, a halogen-containing group, or a combination thereof.

At least one of $X^1$ and $X^2$ may be a hydroxy group.

a, b, and c may be 1, and at least one of $X^3$ and $X^4$ may be a hydroxy group.

a may be 0, b and c may be 1, and at least one of $X^3$ and $X^4$ may be a hydroxy group.

At least one of $C^1$, $D^1$ and $E^1$ may be a substituted or unsubstituted C1 to C30 alkyl group, a substituted or unsubstituted C6 to C30 aryl group, or a combination thereof, and at least one of $C^2$, $D^2$ and $E^2$ may be a substituted or unsubstituted C1 to C30 alkyl group, a substituted or unsubstituted C6 to C30 aryl group, or a combination thereof.

a, b, and c may be 1, at least one of $C^3$, $D^3$ and $E^3$ may be a substituted or unsubstituted C1 to C30 alkyl group, a substituted or unsubstituted C6 to C30 aryl group, or a combination thereof, and at least one of $C^4$, $D^4$ and $E^4$ may be a substituted or unsubstituted C1 to C30 alkyl group, a substituted or unsubstituted C6 to C30 aryl group, or a combination thereof.

c may be 1, and at least one of $A^1$, $A^2$ and $A^3$ may be an aromatic ring group independently substituted with 1 or more methoxy groups or ethoxy groups.

a, b, and c may be 1, and at least one of $A^4$ and $A^5$ may be an aromatic ring group independently substituted with 1 or more methoxy groups or ethoxy groups.

The monomer may have a molecular weight of about 800 to about 5,000.

The embodiments may be realized by providing a polymer including a moiety represented by Chemical Formula 2:

[Chemical Formula 2]

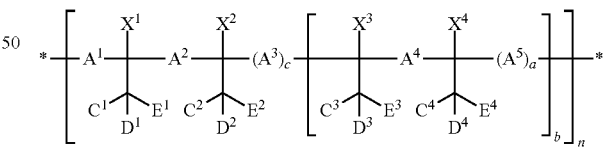

wherein, in Chemical Formula 2, $A^1$, $A^2$, $A^3$, $A^4$, and $A^5$ are each independently a substituted or unsubstituted aromatic ring group, $X^1$, $X^2$, $X^3$, and $X^4$ are each independently a hydroxy group, a substituted or unsubstituted amino group, a halogen atom, a substituted or unsubstituted C1 to C30 alkyl group, a substituted or unsubstituted C6 to C30 aryl group, a substituted or unsubstituted C1 to C30 alkoxy group, a substituted or unsubstituted C3 to C30 cycloalkenyl group, a substituted or unsubstituted C1 to C20 alkylamine group, a substituted or unsubstituted C7 to C20 arylalkyl group, a substituted or unsubstituted C1 to C20 heteroalkyl group, a substituted or unsubstituted C2 to C30 heterocycloalkyl group, a substituted or unsubstituted C2 to C30 heteroaryl group, a substituted or unsubstituted C1 to C4 alkyl ether group, a substituted or unsubstituted C7 to C20 arylalkylene ether group, a substituted or unsubstituted C1 to C30 haloalkyl group, or a combination thereof, $C^1$, $C^2$, $C^3$, $C^4$, $D^1$, $D^2$, $D^3$, $D^4$, $E^1$, $E^2$, $E^3$, and $E^4$ are each independently hydrogen atom, hydroxy group, a substituted or unsubstituted amino group, a halogen atom, a substituted or unsubstituted C1 to C30 alkyl group, a substituted or unsubstituted C6 to C30 aryl group, a substituted or unsubstituted C1 to C30 alkoxy group, a substituted or unsubstituted C3 to C30 cycloalkenyl group, a substituted or unsubstituted C1 to C20 alkylamine group, a substituted or unsubstituted C7 to C20 arylalkyl group, a substituted or unsubstituted C1 to C20 heteroalkyl group, a substituted or unsubstituted C2 to C30 heterocycloalkyl group, a substituted or unsubstituted C2 to C30 heteroaryl group, a substituted or unsubstituted C1 to C4 alkyl ether group, a substituted or unsubstituted C7 to C20 arylalkylene ether group, a substituted or unsubstituted C1 to C30 haloalkyl group, or a combination thereof, a, b, and c are each independently 0 or 1, and n is an integer of 1 to 500.

$A^1$, $A^2$, $A^3$, $A^4$, and $A^5$ may each independently be a substituted or unsubstituted aromatic ring group below:

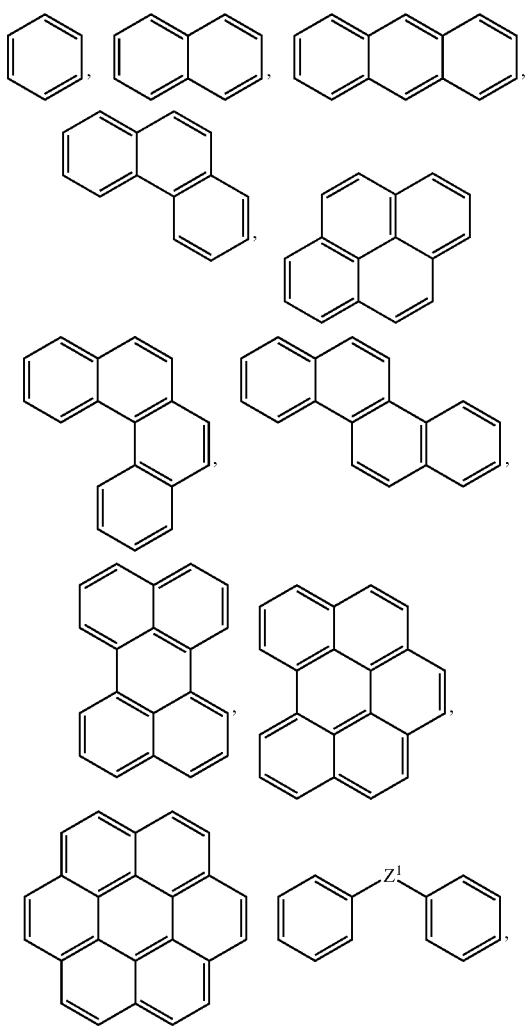
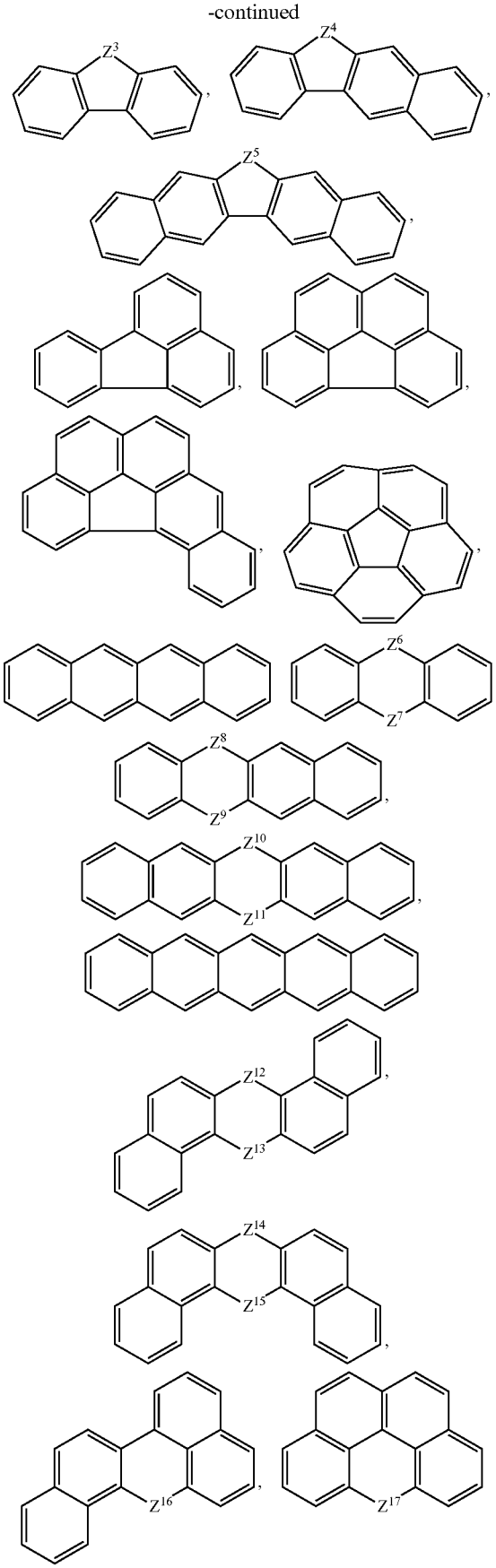

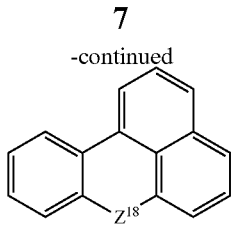

wherein, in the groups above, $Z^1$ may be a single bond, a substituted or unsubstituted C1 to C20 alkylene group, a substituted or unsubstituted C3 to C20 cycloalkylene group, a substituted or unsubstituted C6 to C20 arylene group, a substituted or unsubstituted C2 to C20 heteroarylene group, a substituted or unsubstituted C2 to C20 alkenylene group, a substituted or unsubstituted C2 to C20 alkynylene group, C=O, $NR^a$, oxygen (O), sulfur (S), or a combination thereof, wherein $R^a$ is hydrogen, a substituted or unsubstituted C1 to C10 alkyl group, a substituted or unsubstituted C6 to C20 arylene group, a substituted or unsubstituted C2 to C20 heteroarylene group, a halogen atom, or a combination thereof, and $Z^3$ to $Z^{18}$ may each independently be C=O, $NR^a$, oxygen (O), sulfur (S), $CR^bR^c$, or a combination thereof, in which $R^a$ to $R^c$ are each independently hydrogen, a substituted or unsubstituted C1 to C10 alkyl group, a substituted or unsubstituted C6 to C20 arylene group, a substituted or unsubstituted C2 to C20 heteroarylene group, a halogen atom, a halogen-containing group, or a combination thereof.

At least one of $X^1$ and $X^2$ may be a hydroxy group.

a may be 0, b and c may be 1, and at least one of $X^3$ and $X^4$ may be a hydroxy group.

At least one of $C^1$, $D^1$, and $E^1$ may be a substituted or unsubstituted C1 to C30 alkyl group, a substituted or unsubstituted C6 to C30 aryl group, or a combination thereof, and at least one of $C^2$, $D^2$, and $E^2$ may be a substituted or unsubstituted C1 to C30 alkyl group, a substituted or unsubstituted C6 to C30 aryl group, or a combination thereof.

a may be 0, b and c may be 1, at least one of $C^3$, $D^3$, and $E^3$ may be a substituted or unsubstituted C1 to C30 alkyl group, a substituted or unsubstituted C6 to C30 aryl group, or a combination thereof, and at least one of $C^4$, $D^4$, and $E^4$ may be a substituted or unsubstituted C1 to C30 alkyl group, a substituted or unsubstituted C6 to C30 aryl group, or a combination thereof.

a may be 0, b and c may be 1, and at least one of $A^1$, $A^2$, $A^3$, and $A^4$ may be an aromatic ring group independently substituted with 1 or more methoxy groups or ethoxy groups.

The polymer may have a weight average molecular weight of about 1,000 to about 200,000.

The embodiments may be realized by providing an organic layer composition including a solvent; and the monomer according to an embodiment.

The monomer may be included in an amount of about 0.1 wt % to about 30 wt %, based on a total weight of the organic layer composition.

The embodiments may be realized by providing an organic layer obtained by curing the organic layer composition according to an embodiment.

The organic layer may include a hardmask layer.

The embodiments may be realized by providing a method of forming patterns, the method including providing a material layer on a substrate, applying the organic layer composition as claimed in claim 19 on the material layer, curing the organic layer composition to form a hardmask layer, forming a silicon-containing thin layer on the hardmask layer, forming a photoresist layer on the silicon-containing thin layer, exposing and developing the photoresist layer to form a photoresist pattern, selectively removing the silicon-containing thin layer and the hardmask layer and the hardmask layer using the photoresist pattern to expose a part of the material layer, and etching an exposed part of the material layer.

Applying the organic layer composition may include performing a spin-on coating.

The silicon-containing thin layer may include SiCN, SiOC, SiON, SiOCN, SiC, SiN, or a combination thereof.

The method may further include forming a bottom anti-reflective coating prior to forming the photoresist layer.

The embodiments may be realized by providing an organic layer composition including a solvent; and the polymer according to an embodiment.

The embodiments may be realized by providing a organic layer obtained by curing the organic layer composition according to an embodiment.

DETAILED DESCRIPTION

Example embodiments will now be described more fully hereinafter; however, they may be embodied in different forms and should not be construed as limited to the embodiments set forth herein. Rather, these embodiments are provided so that this disclosure will be thorough and complete, and will fully convey exemplary implementations to those skilled in the art.

It will also be understood that when a layer or element is referred to as being "on" another layer or element, it can be directly on the other element, or intervening elements may also be present. In addition, it will also be understood that when an element is referred to as being "between" two element, it can be the only element between the two elements, or one or more intervening elements may also be present. Like reference numerals refer to like elements throughout.

As used herein, when a definition is not otherwise provided, the term 'substituted' may refer to one substituted with a substituent selected from a halogen atom (F, Br, Cl, or I), a hydroxy group, an alkoxy group, a nitro group, a cyano group, an amino group, an azido group, an amidino group, a hydrazino group, a hydrazono group, a carbonyl group, carbamyl group, a thiol group, an ester group, a carboxyl group or a salt thereof, a sulfonic acid group or a salt thereof, a phosphoric acid or a salt thereof, a C1 to C20 alkyl group, a C2 to C20 alkenyl group, a C2 to C20 alkynyl group, a C6 to C30 aryl group, a C7 to C30 arylalkyl group, a C1 to C30 alkoxy group, a C1 to C20 heteroalkyl group, a C3 to C20 heteroaryl group, a C3 to C30 cycloalkyl group, a C3 to C15 cycloalkenyl group, C6 to C15 cycloalkynyl group, a C2 to C30 heterocycloalkyl group, and a combination thereof.

As used herein, when a definition is not otherwise provided, the term 'hetero' refers to one including 1 to 3 heteroatoms selected from B, N, O, S, and P.

As used herein, when a definition is not otherwise provided, '*' indicates a linking point of a compound or a moiety of a compound to an adjacent atom, moiety, or compound.

Hereinafter, a monomer according to one embodiment is described.

A monomer according to an embodiment may be represented by Chemical Formula 1.

[Chemical Formula 1]

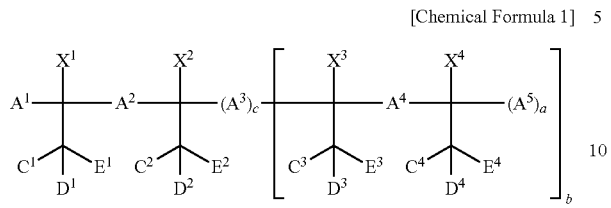

In Chemical Formula 1, $A^1$, $A^2$, $A^3$, $A^4$ and $A^5$ may each independently be or include, e.g., a substituted or unsubstituted aromatic ring group, $X^1$, $X^2$, $X^3$ and $X^4$ may each independently be or include, e.g., a hydroxy group, a substituted or unsubstituted amino group, a halogen atom, a substituted or unsubstituted C1 to C30 alkyl group, a substituted or unsubstituted C6 to C30 aryl group, a substituted or unsubstituted C1 to C30 alkoxy group, a substituted or unsubstituted C3 to C30 cycloalkenyl group, a substituted or unsubstituted C1 to C20 alkylamine group, a substituted or unsubstituted C7 to C20 arylalkyl group, a substituted or unsubstituted C1 to C20 heteroalkyl group, a substituted or unsubstituted C2 to C30 heterocycloalkyl group, a substituted or unsubstituted C2 to C30 heteroaryl group, a substituted or unsubstituted C1 to C4 alkyl ether group, a substituted or unsubstituted C7 to C20 arylalkylene ether group, a substituted or unsubstituted C1 to C30 haloalkyl group, or a combination thereof, $C^1$, $C^2$, $C^3$, C4, $D^1$, $D^2$, $D^3$, $D^4$, $E^1$, $E^2$, $E^3$ and $E^4$ may each independently be or include, e.g., hydrogen atom, hydroxy group, a substituted or unsubstituted amino group, a halogen atom, a substituted or unsubstituted C1 to C30 alkyl group, a substituted or unsubstituted C6 to C30 aryl group, a substituted or unsubstituted C1 to C30 alkoxy group, a substituted or unsubstituted C3 to C30 cycloalkenyl group, a substituted or unsubstituted C1 to C20 alkylamine group, a substituted or unsubstituted C7 to C20 arylalkyl group, a substituted or unsubstituted C1 to C20 heteroalkyl group, a substituted or unsubstituted C2 to C30 heterocycloalkyl group, a substituted or unsubstituted C2 to C30 heteroaryl group, a substituted or unsubstituted C1 to C4 alkyl ether group, a substituted or unsubstituted C7 to C20 arylalkylene ether group, a substituted or unsubstituted C1 to C30 haloalkyl group, or a combination thereof, and a, b, and c may each independently be 0 or 1.

For example, in Chemical Formula 1, a and b may be 0 and c may be 1. For example, in Chemical Formula 1, a, b and c may be 1. For example, when a is 0, the carbon that would be bound to $A^5$ may be bound to hydrogen instead.

The monomer may have a structure including quaternary carbon between two substituted or unsubstituted aromatic ring groups. As used herein, the quaternary carbon is defined as carbon bonded with other groups except for hydrogen which all replace four hydrogens bonded therewith (e.g., a quaternary carbon is not necessarily a carbon atom bonded only to four other carbon atoms).

The monomer has a structure including the quaternary carbon and exhibits improved dissolution. Thus, application of the monomer using a spin-on coating method may be improved.

[Reaction Scheme 1]

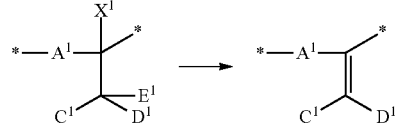

Reaction Scheme 1 exemplarily represents a reaction in which functional groups expressed as $X^1$ and $E^1$ are removed when the monomer is cured at a high temperature. A cured film formed using the monomer according to the reaction may have excellent film density.

In Chemical Formula 1, a functional group represented by $X^1$, $X^2$, $X^3$ and $X^4$ and a functional group represented by $C^1$, $C^2$, $C^3$, $C^4$, $D^1$, $D^2$, $D^3$, $D^4$, $E^1$, $E^2$, $E^3$ and $E^4$ may be eliminated or crystallized by curing the monomer at a high temperature.

In an implementation, in Chemical Formula 1, at least one of $X^1$ and $X^2$ may be a hydroxy group. In an implementation, e.g., when a, b, and c are 1, at least one of $X^3$ and $X^4$ may be a hydroxy group. In an implementation, e.g., when a is 0 and b and c are 1, at least one of $X^3$ and $X^4$ may be a hydroxy group.

For example, in Chemical Formula 1, at least one of $C^1$, $D^1$ and $E^1$ may be a substituted or unsubstituted C1 to C30 alkyl group, a substituted or unsubstituted C6 to C30 aryl group, or a combination thereof, at least one of the $C^2$, $D^2$ and $E^2$ may be a substituted or unsubstituted C1 to C30 alkyl group, a substituted or unsubstituted C6 to C30 aryl group, or a combination thereof. In an implementation, in Chemical Formula 1, when the a, b, and c are 1, at least one of the $C^3$, $D^3$ and $E^3$ may be a substituted or unsubstituted C1 to C30 alkyl group, a substituted or unsubstituted C6 to C30 aryl group, or a combination thereof, and at least one of $C^4$, $D^4$ and $E^4$ may be a substituted or unsubstituted C1 to C30 alkyl group, a substituted or unsubstituted C6 to C30 aryl group, or a combination thereof.

The monomer may include an aromatic ring group and may exhibit rigid characteristics.

In Chemical Formula 1, $A^1$, $A^2$, $A^3$, $A^4$ and $A^5$ (representing a substituted or unsubstituted aromatic ring group) may each independently be selected from one of the following groups.

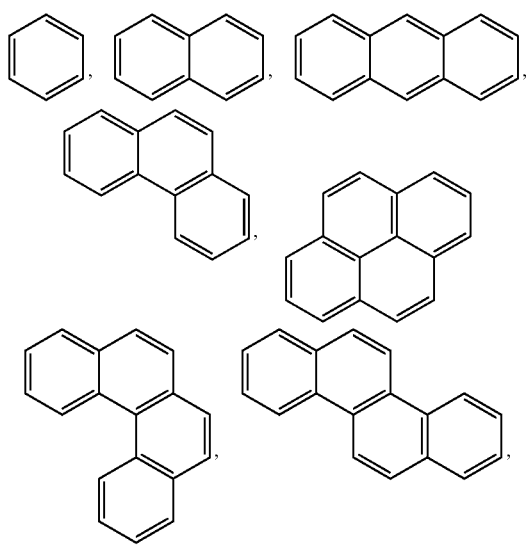

-continued

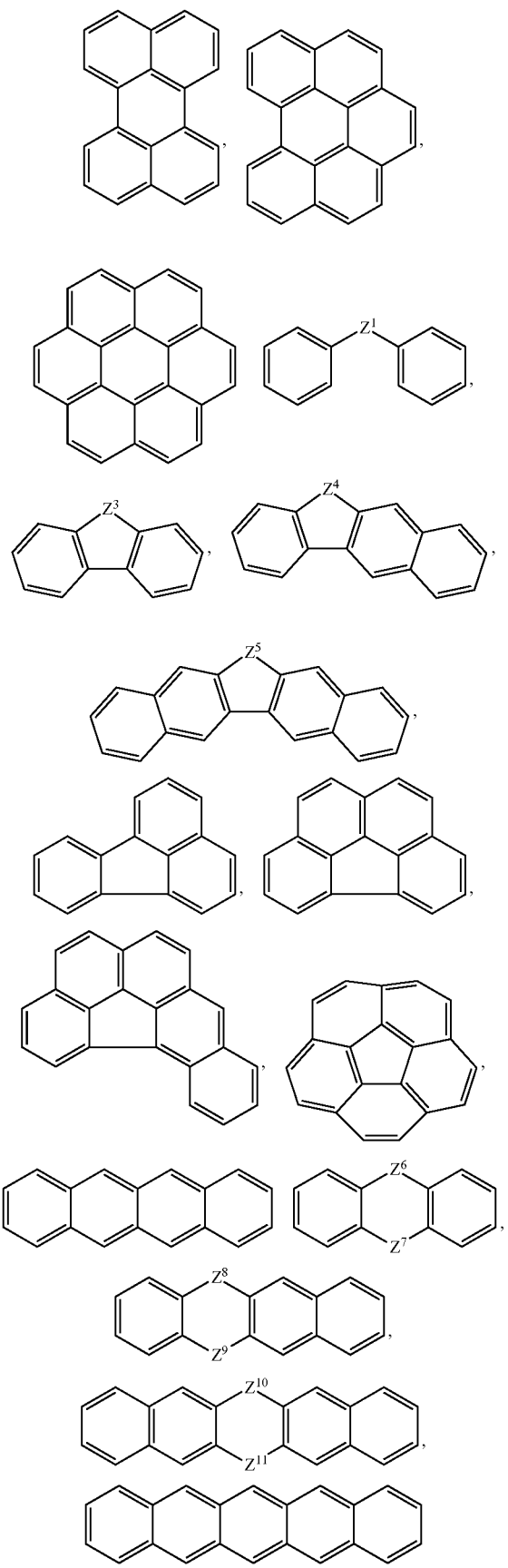

-continued

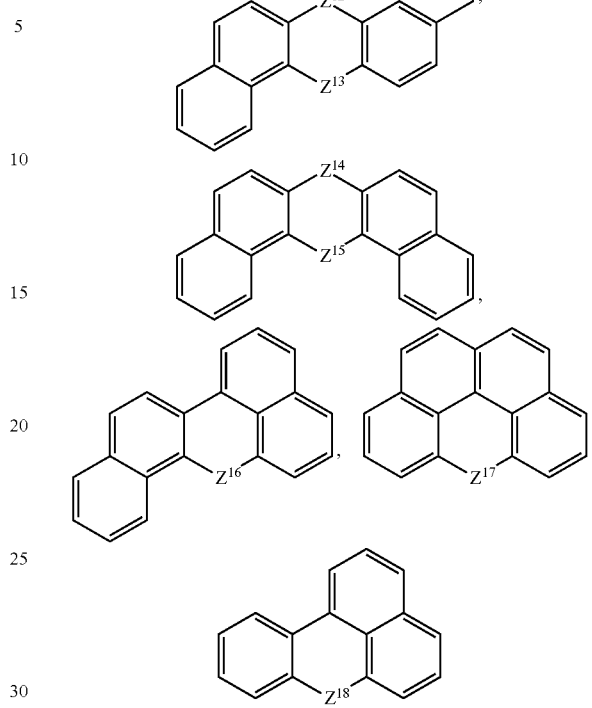

In the groups above, $Z^1$ may be or may include, e.g., a single bond, a substituted or unsubstituted C1 to C20 alkylene group, a substituted or unsubstituted C3 to C20 cycloalkylene group, a substituted or unsubstituted C6 to C20 arylene group, a substituted or unsubstituted C2 to C20 heteroarylene group, a substituted or unsubstituted C2 to C20 alkenylene group, a substituted or unsubstituted C2 to C20 alkynylene group, C=O, $NR^a$, oxygen (O), sulfur (S), or a combination thereof, in which $R^a$ may be or may include hydrogen, a substituted or unsubstituted C1 to C10 alkyl group, a substituted or unsubstituted C6 to C20 arylene group, a substituted or unsubstituted C2 to C20 heteroarylene group, a halogen atom, or a combination thereof, and $Z^3$ to $Z^{18}$ may each independently be, e.g., C=O, $NR^a$, oxygen (O), sulfur (S), $CR^bR^c$ or a combination thereof, in which $R^a$ to $R^c$ may each independently be or include hydrogen, a substituted or unsubstituted C1 to C10 alkyl group, a substituted or unsubstituted C6 to C20 arylene group, a substituted or unsubstituted C2 to C20 heteroarylene group, a halogen atom, a halogen-containing group, or a combination thereof. For example, $A^1, A^2, A^3, A^4$ and $A^5$ may include a substituted or unsubstituted one of the illustrated groups, and may be bound to or between carbon atoms at any suitable position.

For example, in Chemical Formula 1, when c is 1, at least one of $A^1$, $A^2$ and $A^3$ may be an aromatic ring group independently substituted with 1 or more, e.g., 2 or more, methoxy groups (—$OCH_3$) or ethoxy groups (—$OC_2H5$). For example, in Chemical Formula 1, when a, b, and c are 1, at least one of $A^4$ and $A^5$ may be an aromatic ring group independently substituted with 1 or more, e.g., 2 or more, methoxy groups (—$OCH_3$) or ethoxy groups (—$OC_2H5$).

The monomer may have a molecular weight of about 800 to about 5,000. When the monomer has a molecular weight within the above range, solubility of the monomer having a high carbon content in a solvent may be improved, and an improved thin layer may be obtained through spin-on coating.

Hereinafter, a polymer according to another embodiment is described.

A polymer according to another embodiment may have a repeating unit structure, e.g., may include a moiety, represented by Chemical Formula 2.

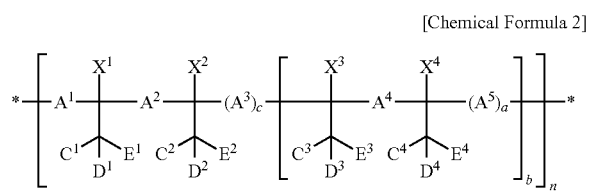

[Chemical Formula 2]

In Chemical Formula 2, $A^1$, $A^2$, $A^3$, $A^4$ and $A^5$ may each independently be or include, e.g., a substituted or unsubstituted aromatic ring group, $X^1$, $X^2$, $X^3$ and $X^4$ may each independently be or include, e.g., a hydroxy group, a substituted or unsubstituted amino group, a halogen atom, a substituted or unsubstituted C1 to C30 alkyl group, a substituted or unsubstituted C6 to C30 aryl group, a substituted or unsubstituted C1 to C30 alkoxy group, a substituted or unsubstituted C3 to C30 cycloalkenyl group, a substituted or unsubstituted C1 to C20 alkylamine group, a substituted or unsubstituted C7 to C20 arylalkyl group, a substituted or unsubstituted C1 to C20 heteroalkyl group, a substituted or unsubstituted C2 to C30 heterocycloalkyl group, a substituted or unsubstituted C2 to C30 heteroaryl group, a substituted or unsubstituted C1 to C4 alkyl ether group, a substituted or unsubstituted C7 to C20 arylalkylene ether group, a substituted or unsubstituted C1 to C30 haloalkyl group, or a combination thereof, $C^1$, $C^2$, $C^3$, $C^4$, $D^1$, $D^2$, $D^3$, $D^4$, $E^1$, $E^2$, $E^3$ and $E^4$ may each independently be or include, e.g., hydrogen atom, hydroxy group, a substituted or unsubstituted amino group, a halogen atom, a substituted or unsubstituted C1 to C30 alkyl group, a substituted or unsubstituted C6 to C30 aryl group, a substituted or unsubstituted C1 to C30 alkoxy group, a substituted or unsubstituted C3 to C30 cycloalkenyl group, a substituted or unsubstituted C1 to C20 alkylamine group, a substituted or unsubstituted C7 to C20 arylalkyl group, a substituted or unsubstituted C1 to C20 heteroalkyl group, a substituted or unsubstituted C2 to C30 heterocycloalkyl group, a substituted or unsubstituted C2 to C30 heteroaryl group, a substituted or unsubstituted C1 to C4 alkyl ether group, a substituted or unsubstituted C7 to C20 arylalkylene ether group, a substituted or unsubstituted C1 to C30 haloalkyl group, or a combination thereof, a, b and c may each independently be 0 or 1, and n may be an integer of 1 to 500.

For example, in Chemical Formula 2, a may be 0, and b and c may be 1.

The polymer may have a structure including quaternary carbon between two substituted or unsubstituted aromatic ring groups. The polymer may include the quaternary carbon in a repeating unit and may exhibit improved dissolution. Thus, the polymer may be better applied in a spin-on coating method.

A functional group removal reaction shown in the aforementioned Reaction Scheme 1 (when cured at a high temperature) may also occur in the polymer, an organic layer formed therefrom may have excellent layer density.

In Chemical Formula 2, functional groups represented by $X^1$, $X^2$, $X^3$ and $X^4$ and functional groups represented by $C^1$, $C^2$, $C^3$, $C^4$, $D^1$, $D^2$, $D^3$, $D^4$, $E^1$, $E^2$, $E^3$ and $E^4$ may be eliminated or cyclized by curing the polymer at a high temperature.

For example, at least one of $X^1$ and $X^2$ in Chemical Formula 2 may be a hydroxy group, and when a is 0, and b and c are 1, at least one of $X^3$ and $X^4$ may be a hydroxy group.

For example, in Chemical Formula 2, $C^1$, and at least one of $D^1$ and $E^1$ may be a substituted or unsubstituted C1 to C30 alkyl group, a substituted or unsubstituted C6 to C30 aryl group, or a combination thereof, and/or at least one of $C^2$, $D^2$ and $E^2$ may be a substituted or unsubstituted C1 to C30 alkyl group, a substituted or unsubstituted C6 to C30 aryl group, or a combination thereof. In an implementation, when a is 0 and b and c are 1, at least one of $C^3$, $D^3$ and $E^3$ may be a substituted or unsubstituted C1 to C30 alkyl group, a substituted or unsubstituted C6 to C30 aryl group, or a combination thereof, and/or at least one of $C^4$, $D^4$ and $E^4$ may be a substituted or unsubstituted C1 to C30 alkyl group, a substituted or unsubstituted C6 to C30 aryl group, or a combination thereof.

The polymer may have improved etch resistance due to the aromatic ring group.

For example, in Chemical Formula 2, $A^1$, $A^2$, $A^3$, $A^4$ and $A^5$ (representing a substituted or unsubstituted aromatic ring group) may each independently be one of the groups described with respect to $A^1$, $A^2$, $A^3$, $A^4$ and $A^5$ of Chemical Formula 1.

For example, in Chemical Formula 2, when a is 0 and b and c are 1, at least one of $A^1$, $A^2$, $A^3$ and $A^4$ may be an aromatic ring group substituted with 1 or more, e.g., 2 or more, methoxy groups ($-OCH_3$) or ethoxy groups ($-OC_2H_5$).

The polymer may be a weight average molecular weight of about 1,000 to about 200,000. When the polymer has a weight average molecular weight within the range, an organic layer composition (e.g., a hardmask composition) including the polymer may be optimized by adjusting the carbon content and solubility in a solvent.

According to an embodiment, an organic layer composition may include a compound for an organic layer (selected from the monomer described above, the polymer described above, or a combination thereof) and a solvent.

The solvent may be a suitable solvent having sufficient dissolubility or dispersion for the compound for an organic layer. The solvent may include, e.g., propylene glycol, propylene glycol diacetate, methoxy propanediol, diethylene glycol, diethylene glycol butylether, tri(ethylene glycol) monomethylether, propylene glycol monomethylether, propylene glycol monomethylether acetate, cyclohexanone, ethyllactate, gamma-butyrolactone, N,N-dimethyl formamide, N,N-dimethyl acetamide, methylpyrrolidone, methylpyrrolidinone, acetylacetone, or ethyl 3-ethoxypropionate.

The compound for an organic layer (e.g., the monomer and/or the polymer) may be included in an amount of about 0.1 to about 30 wt %, based on a total weight of the organic layer composition. When the compound for an organic layer is included in the range, a thickness, surface roughness and planarization of the organic layer may be controlled.

The organic layer composition may further include an additive, e.g., a surfactant, a cross-linking agent, a thermal acid generator, a photoacid generator, a plasticizer, or the like.

The surfactant may include, e.g., alkylbenzene sulfonate salt, alkyl pyridinium salt, polyethylene glycol, or a quaternary ammonium salt.

The cross-linking agent may include, e.g., a melamine-based, a substituted urea-based, or a polymer-based agent thereof. In an implementation, a cross-linking agent having at least two cross-linking forming substituent may include, e.g., a compound such as methoxymethylated glycoluril, butoxymethylated glycoluril, methoxymethylated melamine, butoxymethylated melamine, methoxymethylated benzoguanamine, butoxymethylated benzoguanamine, methoxymethylated urea, butoxymethylated urea, methoxymethylated thiourea, methoxymethylated thiourea, or the like.

In addition, the cross-linking agent may have high heat resistance. The cross-linking agent having high heat resistance may be a compound containing a cross-linking substituent having an aromatic ring (for example, a benzene ring, a naphthalene ring) in its molecule.

The thermal acid generator may include, e.g., an acidic compound such as p-toluenesulfonic acid, trifluoromethanesulfonic acid, pyridiniump-toluenesulfonic acid, salicylic acid, sulfosalicylic acid, citric acid, benzoic acid, hydroxybenzoic acid, naphthalenecarbonic acid and the like or/and 2,4,4,6-tetrabromocyclohexadienone, benzointosylate, 2-nitrobenzyltosylate, other organosulfonic acid alkylester, or the like.

The photoacid generator may include, e.g., triphenylsulfonium triflate, triphenylsulfonium antimonate, diphenyliodonium triflate, diphenyliodonium antimonate, methoxydiphenyliodonium triflate, di-t-butyldiphenyliodonium triflate, 2,6-dinitrobenzyl sulfonate, pyrogallol tris(alkylsulfonate), N-hydroxysuccinimide triflate, norbornene-dicarboximide-triflate, triphenylsulfonium nonaflate, diphenyliodonium nonaflate, methoxydiphenyliodonium nonaflate, di-t-butyldiphenyliodonium nonaflate, N-hydroxysuccinimide nonaflate, norbornene-dicarboximide-nonaflate, triphenylsulfonium perfluorobutanesulfonate, triphenylsulfonium perfluorooctanesulfonate (PFOS), diphenyliodonium (PFOS), methoxydiphenyliodonium PFOS, di-t-butyldiphenyliodonium triflate, N-hydroxysuccinimide PFOS, norbornene-dicarboximide PFOS, or a combination thereof.

The plasticizer may include, e.g., DOP (dioctylphthalate), DOA (dioctyl adipate), TCP (tricresyl phosphate), DIOP (diisocctyl phthalate), DL79P (diheptyl, nonyl phthalate) DINP (diisononyl phthalate), DUP (diunedcyl phthalate), BBP (butyl benzyl phthalate), DOA (di-2-ethyl hexyl adipate), DIDA (diisodecyl adipate), DOZ (di-2-ethylhexyl Sebacate), DIOZ (diisooctyl Azelate), DOS (Di-2-ethylhexyl Sebacate), TOP (tri-2ethylhexyl phosphate), TTP (triphenyl phosphate), CDP (cresyldephenyl phosphate), TCP (tircresyl phosphate), TXP (trixylyl phosphate), TOTM (tri-2-ethylhexyl trimellitate), polyethylene gpycol ester, ASE (alkylsulphonic acid phenyl ester), 3G6 (triethylene glycol dihexanoate), 4G7 (tetraethylene glycol diheptanoate), ATEC (acetyl triethyl citrate), TBC (tributyl citrate), TOC (trioctyl citrate), ATOC (acetyl trioctyl citrate), ATHC (acetyl trihexyl citrate), TMC (trimethyl citrate), DMAD (dimethyl adipate, MMAD (monomethyl adipate), DBM (dibutyl maleate), DIBM (diisobutyl maleate), BDNPF (bis (2,2-dinitropropyl)formal), TNEN (2,2,2-trinitroethyl 2-nitroxyethyl ether), polyethylene glycol, polypropylene, or a combination thereof.

The additive may be included in an amount of about 0.001 to about 40 parts by weight, based on 100 parts by weight of the organic layer composition. When the additive is included within the range, solubility may be improved without changing optical properties of the organic layer composition.

According to another embodiment, an organic layer manufactured using the organic layer composition may be provided. The organic layer may be, e.g., formed by coating the organic layer composition on a substrate and heat-treating it for curing and may include, for example, a hardmask layer, a planarization layer, a sacrificial layer, a filler, or the like for an electronic device.

Hereafter, a method for forming patterns by using the organic layer composition is described.

A method of forming patterns according to an embodiment may include providing a material layer on a substrate, applying the organic layer composition, curing the organic layer composition to form a hardmask layer, forming a silicon-containing thin layer on the hardmask layer, forming a photoresist layer on the silicon-containing thin layer, exposing and developing the photoresist layer to form a photoresist pattern, selectively removing the silicon-containing thin layer and the hardmask layer using the photoresist pattern to expose a part of the material layer, and etching an exposed part of the material layer.

The substrate may be, e.g., a silicon wafer, a glass substrate, or a polymer substrate.

The material layer is a material to be finally patterned, e.g., a metal layer (such as an aluminum layer or a copper layer), a semiconductor layer (such as a silicon layer), or an insulation layer (such as a silicon oxide layer or a silicon nitride layer). The material layer may be formed through, e.g., a chemical vapor deposition (CVD) process.

The organic layer composition is the same as described above, e.g., according to an embodiment, and may be applied by spin-on coating in a form of a solution. In an implementation, a thickness of the deposited organic layer composition may be, e.g., about 50 Å to about 10,000 Å.

Curing the organic layer composition may be performed by applying energy such as thermal energy, photoenergy, or the like. In an implementation, when the applied energy is thermal energy, the curing may be performed by heat-treating, e.g., at about 100 to about 500° C. for about 10 seconds to about 1 hour.

The silicon-containing thin layer may be formed of, e.g., SiCN, SiOC, SiON, SiOCN, SiC, SiN, or a combination thereof.

The method may further include forming a bottom anti-reflective coating (BARC) before forming the photoresist layer.

Exposure of the photoresist layer may be performed using, e.g., ArF, KrF, or EUV. After exposure, heat treatment may be performed at about 100° C. to about 500° C.

The etching process of the exposed part of the material layer may be performed through a dry etching process using an etching gas and the etching gas may be, e.g., $CHF_3$, $CF_4$, $Cl_2$, $BCl_3$, and a mixed gas thereof.

The etched material layer may be formed in a plurality of pattern, and the plurality of pattern may include a metal pattern, a semiconductor pattern, an insulation pattern, and the like. For example, the patterns may include diverse patterns of a semiconductor integrated circuit device.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

SYNTHESIS EXAMPLES

Synthesis Example 1

Substituent Introduction Reaction 34 g (0.1345 mol) of naphthalene-2,6-dicarbonyldichloride, 62.4 g (0.269 mol) of methoxypyrene, and 496 g of a mixed solution of 1,2-dichloroethane/chloroform were put in a flask. Then, 35.8 g (0.269 mol) of aluminum chloride was slowly added to the solution, and the resulting mixture was agitated at ambient temperature for 12 hours. When the reaction was complete, methanol was added thereto, and a precipitate produced therein was filtered and dried.

Addition Reaction 6.4 g (10 mmol) of the compound obtained from the Substituent Introduction Reaction and 285 g of tetrahydrofuran were put in a flask, 20 ml (40 mol) of benzyl magnesium chloride (2.0 M in THF) was slowly added thereto at 0° C., and the mixture was heated up to ambient temperature and agitated for 24 hours. When the reaction was complete, the resultant was neutralized to about pH 7 with a 5% hydrochloric acid solution and then, extracted and dried with ethyl acetate, obtaining a compound represented by Chemical Formula A.

[Chemical Formula A]

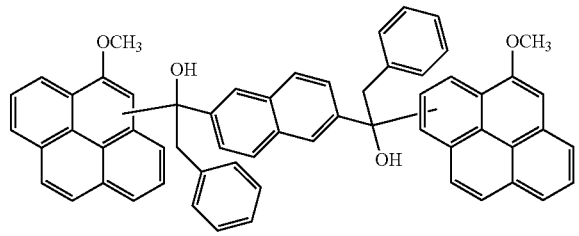

Synthesis Example 2

Substituent Introduction Reaction 28 g (0.1 mol) of benzoperylene, 46 g (0.21 mol) of 6-methoxy-2-naphthoyl chloride, 29 g (0.22 mol) of aluminum chloride and 707 g of dichloromethane were reacted according to the same method as Synthesis Example 1.

Addition Reaction 6.4 g (10 mmol) of the compound obtained from the Substituent Introduction Reaction and 12.5 ml (25 mmol) of isopropylmagnesium chloride (2.0 M in THF) were used according to the same method as Synthesis Example 1, obtaining a compound represented by Chemical Formula B.

[Chemical Formula B]

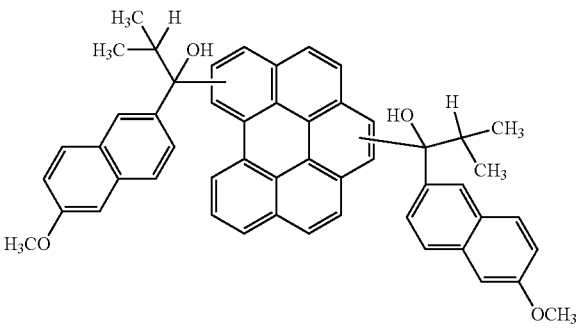

Synthesis Example 3

Substituent Introduction Reaction 20.2 g (0.1 mol) of terephthaloyl dichloride, 11.6 g (0.05 mol) of 4-methoxypyrene, 7.9 g (0.05 mol) of methoxynaphthalene and 157 g of 1,2-dichloroethane were put in a flask. Then, 13.2 g (0.1 mol) of aluminum chloride was slowly added to the solution, and the mixture was agitated at ambient temperature. When a specimen was taken from the polymerization reactant by every hour had a weight average molecular weight ranging from 1,200 to 1,500, the reaction was completed. When the reaction was complete, a precipitate produced by adding methanol thereto was filtered, and a monomer remaining therein was removed with water and methanol, obtaining a polymer represented by Chemical Formula C (Mw: 1500).

[Chemical Formula C]

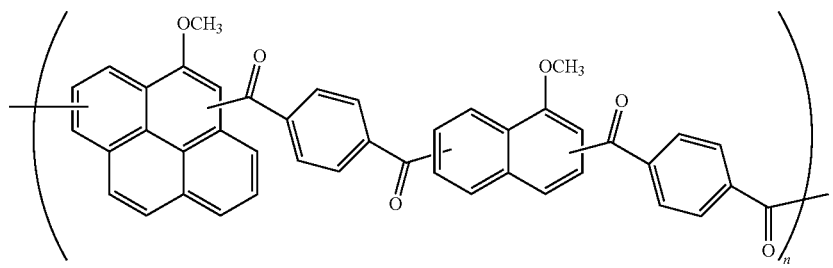

Addition Reaction 7 g of the polymer represented by Chemical Formula C (obtained from the Substituent Introduction Reaction) and 285 g of tetrahydrofuran were put in a flask, 20 ml (40 mol) of benzyl magnesium chloride (2.0 M in THF) was slowly added thereto at 0° C., and the mixture was heated up to ambient temperature and agitated for 24 hours. When the reaction was complete, the resultant was neutralized t about pH 7 with a 5% hydrochloric acid solution and then, extracted with ethyl acetate and dried, obtaining a polymer represented by Chemical Formula D.

[Chemical Formula D]

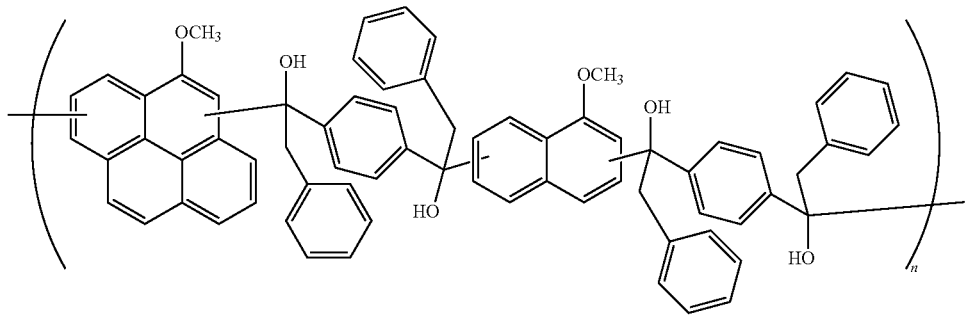

Synthesis Example 4

Substituent Introduction Reaction 21.24 g (0.105 mol) of pyrene and 17.06 g (0.1 mol) of methoxybenzoyl chloride along with 370 g of dichloromethane were put in a 1 L 3-necked flask and agitated for a reaction with a stirring bar, while 14.67 g (0.11 mol) trichloro aluminum was added thereto little by little at ambient temperature. After checking whether the reaction was complete while the mixture was agitated for 1 hour, 10.15 g (0.05 mol) of terephthaloyl chloride was added thereto, and the mixture was reacted while 29.33 g (0.22 mol) of trichloro aluminum was little by little added thereto. Herein, the reaction was performed in an ice bath for 3 hours to control exothermicity. When the reaction was complete, the resultant was added to water, and a reactant obtained as powder (a compound represented by Chemical Formula E) was filtered and dried.

[Chemical Formula E]

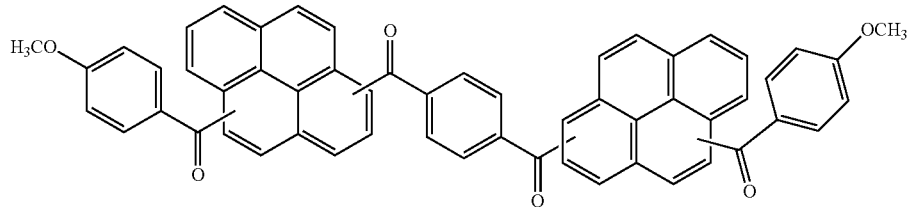

Addition Reaction 8.6 g of the compound represented by Chemical Formula E (obtained from the Substituent Introduction Reaction) and 285 g of tetrahydrofuran were put in a flask, 20 ml (40 mol) of isopropylmagnesium chloride (2.0 M in THF) was slowly added thereto at 0° C., and the mixture was heated up to ambient temperature and agitated for 24 hours. When the reaction was complete, the resultant was neutralized to about pH 7 with a 5% hydrochloric acid solution and then, extracted with ethyl acetate and dried, obtaining a compound represented by Chemical Formula F.

[Chemical Formula F]

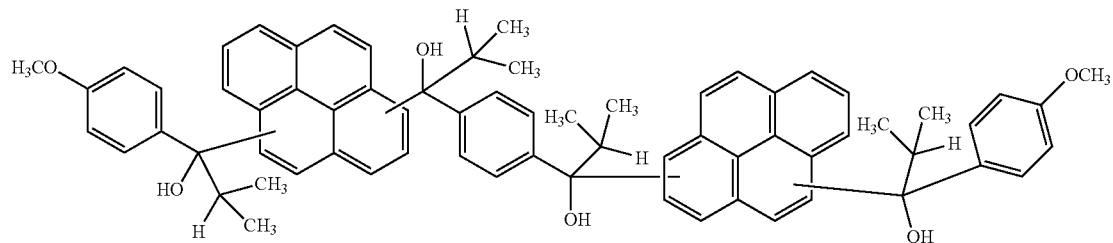

Comparative Synthesis Example 1

21.6 g (0.057 mol) of 9,9-bis(4-methoxyphenyl)-9H-fluorene and 9.6 g (0.057 mol) of 1,4-bis(methoxymethyl)benzene were sequentially put in a 500 ml flask equipped with a thermometer, a condenser and a mechanical agitator, and 51 g of propylene glycol monomethyl ether acetate (PGMEA) was dissolved therein. Then, 0.15 g (0.001 mol) of diethyl sulfite was added thereto, and the mixture was agitated at 90 to 120° C. for 5 to 10 hours or so. When a specimen taken from the polymerization reactant by every hour had a weight average molecular weight ranging from 1,800 to 2,300, the reaction was completed.

When the polymerization reaction was complete, the resultant was subsequently cooled down to ambient temperature and put in 40 g of distilled water and 400 g of methanol, and the mixture was strongly agitated and then, allowed to stand. After removing a supernatant therefrom, a precipitate produced therein was dissolved in 80 g of propylene glycol monomethyl ether acetate (PGMEA), and the solution was strongly agitated with 40 g of methanol and 40 g of water and then, allowed to stand (primary). Herein, after removing the obtained supernatant again, a precipitate produced therein was dissolved in 40 g of propylene glycol monomethyl ether acetate (PGMEA) (secondary). The primary and secondary processes were regarded as a one purification process, and this purification process was performed three times in total. The purified polymer was dissolved in 80 g of propylene glycol monomethyl ether acetate (PGMEA), and methanol and distilled water remaining in the solution were removed under a reduced pressure, obtaining a polymer represented by Chemical Formula G (a weight average molecular weight (Mw)=2,500).

[Chemical Formula G]

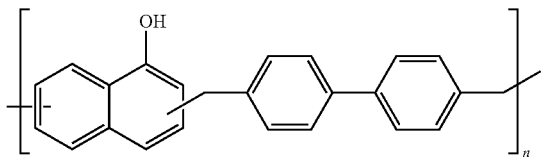

Comparative Synthesis Example 2

28.83 g (0.2 mol) of naphthalen-1-ol, 48.46 g (0.2 mol) of 4,4'-bis(methoxymethyl)biphenyl, 53 g of propylene glycol monomethyl ether acetate (PGMEA) and 1.23 g (8 mmol) of diethylsulfate were used according to the same method as Comparative Synthesis Example 1, obtaining a polymer represented by Chemical Formula H (a weight average molecular weight (Mw)=4300).

[Chemical Formula H]

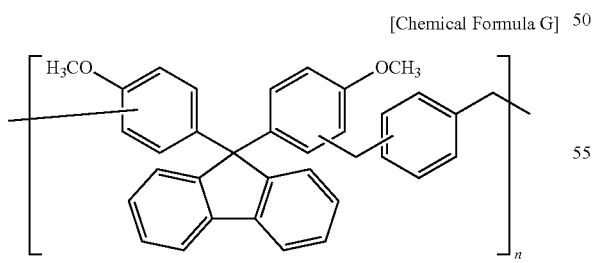

Preparation of Hardmask Composition

Example 1

The compound according to Synthesis Example 1 was dissolved in a mixed solvent of propylene glycolmonomethyl ether acetate (PGMEA) and cyclohexanone (7:3 (v/v)), and the solution was filtered, preparing a hardmask composition. The amount of the compound was adjusted depending on a desired thickness.

Example 2

A hardmask composition was prepared according to the same method as Example 1 except for using the compound according to Synthesis Example 2 instead of the compound according to Synthesis Example 1.

Example 3

A hardmask composition was prepared according to the same method as Example 1 except for using the compound according to Synthesis Example 3 instead of the compound according to Synthesis Example 1.

Example 4

A hardmask composition was prepared according to the same method as Example 1 except for using the compound according to Synthesis Example 4 instead of the compound according to Synthesis Example 1.

Comparative Example 1

A hardmask composition was prepared according to the same method as Example 1 except for using the compound according to Comparative Synthesis Example 1 instead of the compound according to Synthesis Example 1.

Comparative Example 2

A hardmask composition was prepared according to the same method as Example 1 except for using the compound according to Comparative Synthesis Example 1 instead of the compound according to Synthesis Example 2.

Evaluation

Evaluation 1: Etch Resistance

Each hardmask composition (a compound content: 12 to 15 wt %) according to Examples 1 to 4 and Comparative Examples 1 to 2 was respectively spin-on coated to be 4,000 Å thick on a silicon wafer and then, heat-treated on a hot plate at 400° C. for 2 minutes, forming each thin film. Subsequently, the thickness of the thin film was measured. The thin film was dry-etched by using $CHF_3/CF_4$ mixed gas and $N_2/O_2$ mixed gas respectively for 100 seconds and 60 seconds, and then, the thickness of the thin film was measured again. The thicknesses of the thin film before and after the dry etching and etching time were used to calculate a bulk etch rate (BER) according to the following Calculation Equation 1.

(Thickness of initial thin film−Thickness of thin film after etching)/Etching time (Å/s)  [Calculation Equation 1]

The results are shown in Table 1.

TABLE 1

|  | Bulk etch rate (Å/sec) | |
| --- | --- | --- |
|  | $CHF_3/CF_4$ mixed gas | $N_2/O_2$ mixed gas |
| Example 1 | 23.2 | 22.3 |
| Example 2 | 22.6 | 21.4 |
| Example 3 | 23.9 | 22.7 |
| Example 4 | 23.0 | 21.5 |
| Comparative Example 1 | 30.2 | 28.4 |
| Comparative Example 2 | 29.3 | 27.6 |

Referring to Table 1, each thin film formed of the hardmask compositions according to Examples 1 to 4 showed sufficient etch resistance against etching gas and thus, improved bulk etch characteristics, compared with each thin film formed of the hardmask compositions according to Comparative Examples 1 to 2.

By way of summation and review, according to small-sizing the pattern to be formed, it may be difficult to provide a fine pattern having an excellent profile by using some lithographic techniques. Accordingly, a layer, called a hardmask layer, may be formed between the material layer and the photoresist layer to provide a fine pattern. The hardmask layer may play a role of an intermediate layer for transferring the fine pattern of photoresist to the material layer through the selective etching process. Accordingly, the hardmask layer may have characteristics such as heat resistance and etch resistance, and the like to be tolerated during the multiple etching processes. Forming a hardmask layer by a spin-on coating method instead of the chemical vapor deposition has been considered. The spin-on coating method may be easy to perform and may also help improve gap-fill characteristics and planarization characteristics. The gap-fill characteristics of filling a pattern with the layer without a space may be beneficial when multiple patterns are necessarily used to realize a fine pattern. In addition, the planarization characteristics of planarizing the surface of the layer with a lower layer may be beneficial when a substrate has a bump, or a wafer as the substrate has both a pattern-dense region and no pattern region. The embodiments may provide an organic layer material developed with a view toward the above-described characteristics.

The embodiments may provide a monomer simultaneously exhibiting etch resistance and planarization characteristics.

The embodiments may provide a polymer simultaneously exhibiting etch resistance and planarization characteristics.

The embodiments may provide an organic layer simultaneously exhibiting etch resistance and planarization characteristics.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A monomer having Chemical Formula 1:

[Chemical Formula 1]

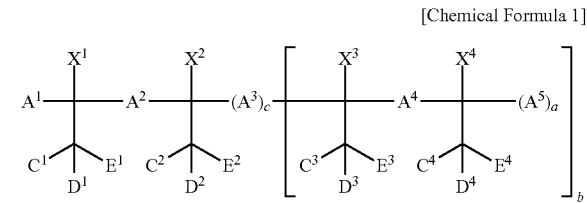

wherein, in Chemical Formula 1, $A^1$, $A^2$, $A^3$, $A^4$, and $A^5$ are each independently a substituted or unsubstituted aromatic ring group, $X^1$, $X^2$, $X^3$, and $X^4$ are each independently a hydroxy group, a substituted or unsubstituted amino group, a halogen atom, a substituted or unsubstituted C1 to C30 alkyl group, a substituted or unsubstituted C6 to C30 aryl group, a substituted or unsubstituted C1 to C30 alkoxy group, a substituted or unsubstituted C3 to C30 cycloalkenyl group, a substituted or unsubstituted C1 to C20 alkylamine group, a substituted or unsubstituted C7 to C20 arylalkyl group, a substituted or unsubstituted C1 to C20 heteroalkyl group, a substituted or unsubstituted C2 to C30 heterocycloalkyl group, a substituted or unsubstituted C2 to C30 heteroaryl group, a substituted or unsubstituted C1 to C4 alkyl ether group, a substituted or unsubstituted C7 to C20 arylalkylene ether group, a substituted or unsubstituted C1 to C30 haloalkyl group, or a combination thereof, $C^1$, $C^2$, $C^3$, $C^4$, $D^1$, $D^2$, $D^3$, $D^4$, $E^1$, $E^2$, $E^3$, and $E^4$ are each independently a hydrogen atom, a hydroxy group, a substituted or unsubstituted amino group, a halogen atom, a substituted or unsubstituted C1 to C30 alkyl group, a substituted or unsubstituted C6 to C30 aryl group, a substituted or unsubstituted C1 to C30 alkoxy group, a substituted or unsubstituted C3 to C30 cycloalkenyl group, a substituted or unsubstituted C1 to C20 alkylamine group, a substituted or unsubstituted C7 to C20 arylalkyl group, a substituted or unsubstituted C1 to C20 heteroalkyl group, a substituted or unsubstituted C2 to C30 heterocycloalkyl group, a substituted or unsubstituted C2 to C30 heteroaryl group, a substituted or unsubstituted C1 to C4 alkyl ether group, a substituted or unsubstituted C7 to C20 arylalkylene ether group, a substituted or unsubstituted C1 to C30 haloalkyl group, or a combination thereof, and a and b are each independently 0 or 1, and c is 1, and wherein:

at least one of $C^1$, $D^1$ and $E^1$ is a substituted or unsubstituted C1 to C30 alkyl group, a substituted or unsubstituted C6 to C30 aryl group, or a combination thereof, and at least one of $C^2$, $D^2$ and $E^2$ is a substituted or unsubstituted C1 to C30 alkyl group, a substituted or unsubstituted C6 to C30 aryl group, or a combination thereof, and at least one of $A^1$, $A^2$ and $A^3$ is an aromatic ring group independently substituted with 1 or more methoxy groups or ethoxy groups.

2. The monomer as claimed in claim 1, wherein $A^1$, $A^2$, $A^3$, $A^4$ and $A^5$ are each independently a substituted or unsubstituted aromatic ring group below:

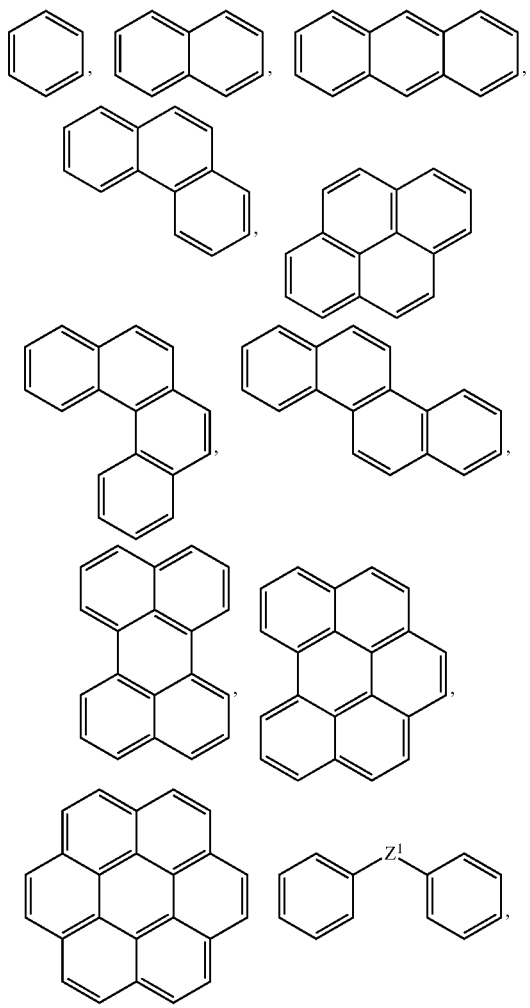

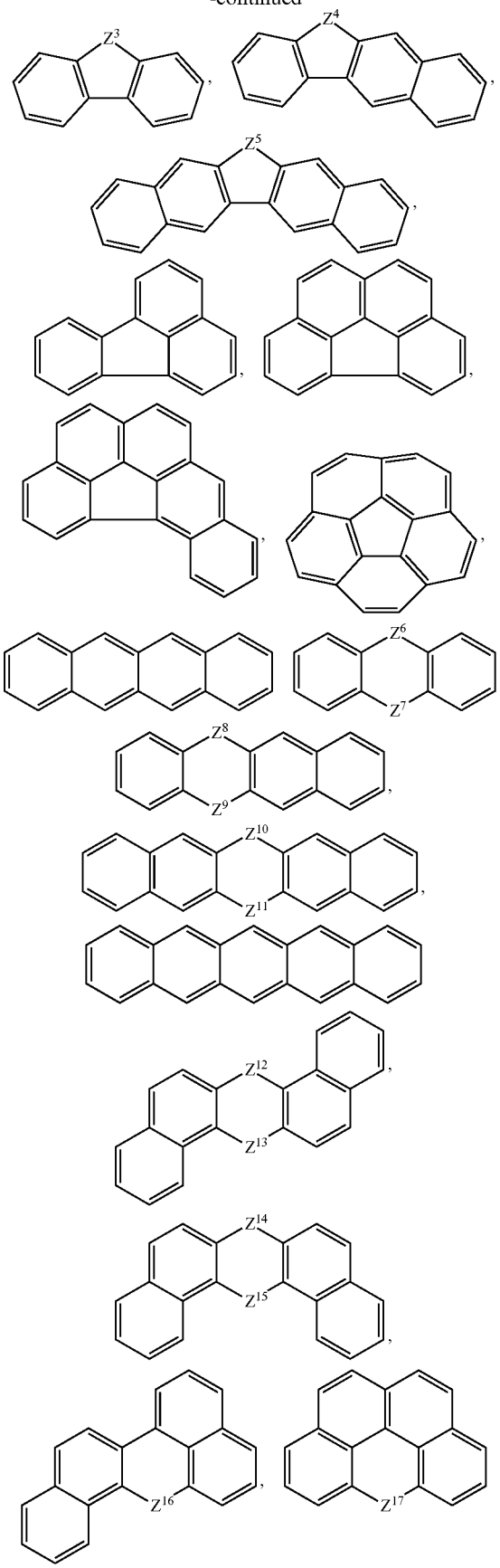

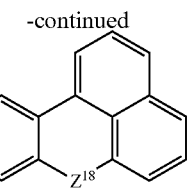

wherein, in the groups above, $Z^1$ is a single bond, a substituted or unsubstituted C1 to C20 alkylene group, a substituted or unsubstituted C3 to C20 cycloalkylene group, a substituted or unsubstituted C6 to C20 arylene group, a substituted or unsubstituted C2 to C20 heteroarylene group, a substituted or unsubstituted C2 to C20 alkenylene group, a substituted or unsubstituted C2 to C20 alkynylene group, C=O, $NR^a$, oxygen (O), sulfur (S), or a combination thereof, wherein $R^a$ is hydrogen, a substituted or unsubstituted C1 to C10 alkyl group, a substituted or unsubstituted C6 to C20 arylene group, a substituted or unsubstituted C2 to C20 heteroarylene group, a halogen atom, or a combination thereof, $Z^3$ to $Z^{18}$ are each independently C=O, $NR^a$, oxygen (O), sulfur (S), $CR^bR^c$ or a combination thereof, in which $R^a$ to $R^c$ are each independently hydrogen, a substituted or unsubstituted C1 to C10 alkyl group, a substituted or unsubstituted C6 to C20 arylene group, a substituted or unsubstituted C2 to C20 heteroarylene group, a halogen atom, a halogen-containing group, or a combination thereof.

3. The monomer as claimed in claim 1, wherein at least one of $X^1$ and $X^2$ is a hydroxy group.

4. The monomer as claimed in claim 3, wherein:

a, b, and c are 1, and at least one of $X^3$ and $X^4$ is a hydroxy group.

5. The monomer as claimed in claim 3, wherein:

a is 0, b and c are 1, and at least one of $X^3$ and $X^4$ is a hydroxy group.

6. The monomer as claimed in claim 1, wherein:

a, b, and c are 1, at least one of $C^3$, $D^3$ and $E^3$ is a substituted or unsubstituted C1 to C30 alkyl group, a substituted or unsubstituted C6 to C30 aryl group, or a combination thereof, and at least one of $C^4$, $D^4$ and $E^4$ is a substituted or unsubstituted C1 to C30 alkyl group, a substituted or unsubstituted C6 to C30 aryl group, or a combination thereof.

7. The monomer as claimed in claim 1, wherein:

a, b, and c are 1, and at least one of $A^4$ and $A^5$ is an aromatic ring group independently substituted with 1 or more methoxy groups or ethoxy groups.

8. The monomer as claimed in claim 1, wherein the monomer has a molecular weight of about 800 to about 5,000.

9. A polymer prepared by polymerizing the monomer as claimed in claim 1, the polymer including a moiety having Chemical Formula 2:

[Chemical Formula 2]

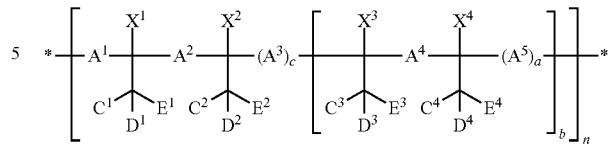

wherein, in Chemical Formula 2, $A^1$, $A^2$, $A^3$, $A^4$, and $A^5$ are each independently a substituted or unsubstituted aromatic ring group, $X^1$, $X^2$, $X^3$, and $X^4$ are each independently a hydroxy group, a substituted or unsubstituted amino group, a halogen atom, a substituted or unsubstituted C1 to C30 alkyl group, a substituted or unsubstituted C6 to C30 aryl group, a substituted or unsubstituted C1 to C30 alkoxy group, a substituted or unsubstituted C3 to C30 cycloalkenyl group, a substituted or unsubstituted C1 to C20 alkylamine group, a substituted or unsubstituted C7 to C20 arylalkyl group, a substituted or unsubstituted C1 to C20 heteroalkyl group, a substituted or unsubstituted C2 to C30 heterocycloalkyl group, a substituted or unsubstituted C2 to C30 heteroaryl group, a substituted or unsubstituted C1 to C4 alkyl ether group, a substituted or unsubstituted C7 to C20 arylalkylene ether group, a substituted or unsubstituted C1 to C30 haloalkyl group, or a combination thereof, $C^1$, $C^2$, $C^3$, $C^4$, $D^1$, $D^2$, $D^3$, $D^4$, $E^1$, $E^2$, $E^3$, and $E^4$ are each independently a hydrogen atom, a hydroxy group, a substituted or unsubstituted amino group, a halogen atom, a substituted or unsubstituted C1 to C30 alkyl group, a substituted or unsubstituted C6 to C30 aryl group, a substituted or unsubstituted C1 to C30 alkoxy group, a substituted or unsubstituted C3 to C30 cycloalkenyl group, a substituted or unsubstituted C1 to C20 alkylamine group, a substituted or unsubstituted C7 to C20 arylalkyl group, a substituted or unsubstituted C1 to C20 heteroalkyl group, a substituted or unsubstituted C2 to C30 heterocycloalkyl group, a substituted or unsubstituted C2 to C30 heteroaryl group, a substituted or unsubstituted C1 to C4 alkyl ether group, a substituted or unsubstituted C7 to C20 arylalkylene ether group, a substituted or unsubstituted C1 to C30 haloalkyl group, or a combination thereof, a and b are each independently 0 or 1, and c is 1, and n is an integer of 1 to 500, and wherein:

at least one of $C^1$, $D^1$ and $E^1$ is a substituted or unsubstituted C1 to C30 alkyl group, a substituted or unsubstituted C6 to C30 aryl group, or a combination thereof, and at least one of $C^2$, $D^2$ and $E^2$ is a substituted or unsubstituted C1 to C30 alkyl group, a substituted or unsubstituted C6 to C30 aryl group, or a combination thereof, and at least one of $A^1$, $A^2$, $A^3$, and $A^4$ is an aromatic ring group independently substituted with 1 or more methoxy groups or ethoxy groups.

10. The polymer as claimed in claim 9, wherein $A^1$, $A^2$, $A^3$, $A^4$, and $A^5$ are each independently a substituted or unsubstituted aromatic ring group below:

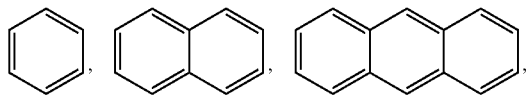

-continued

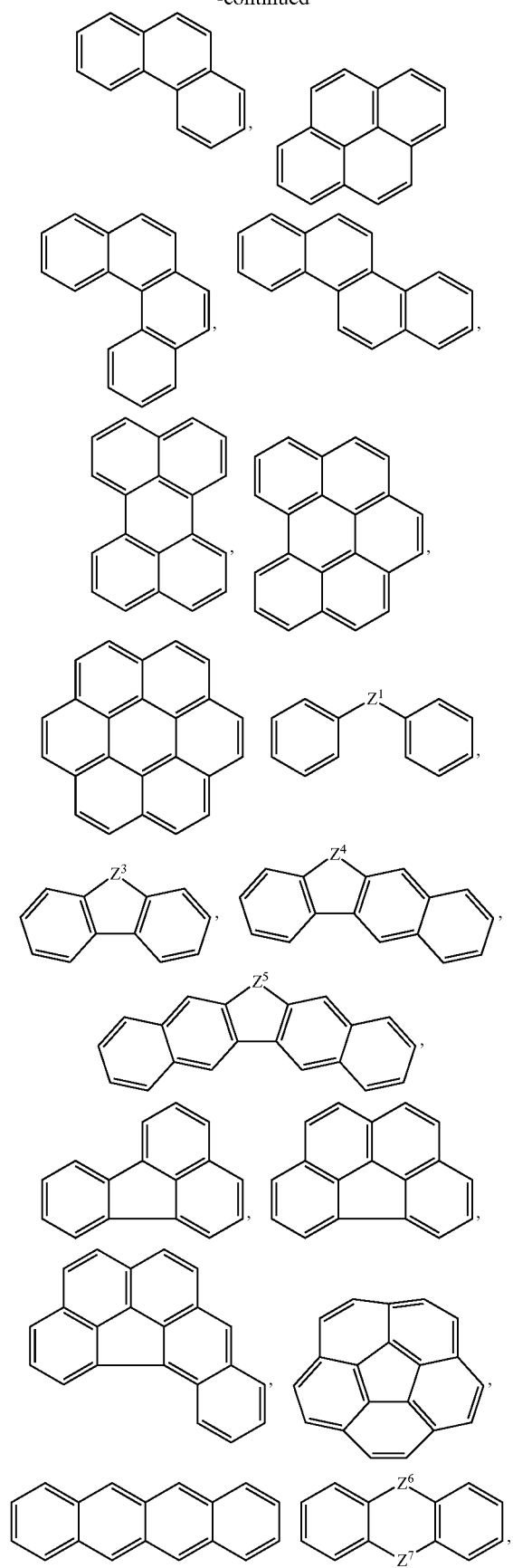

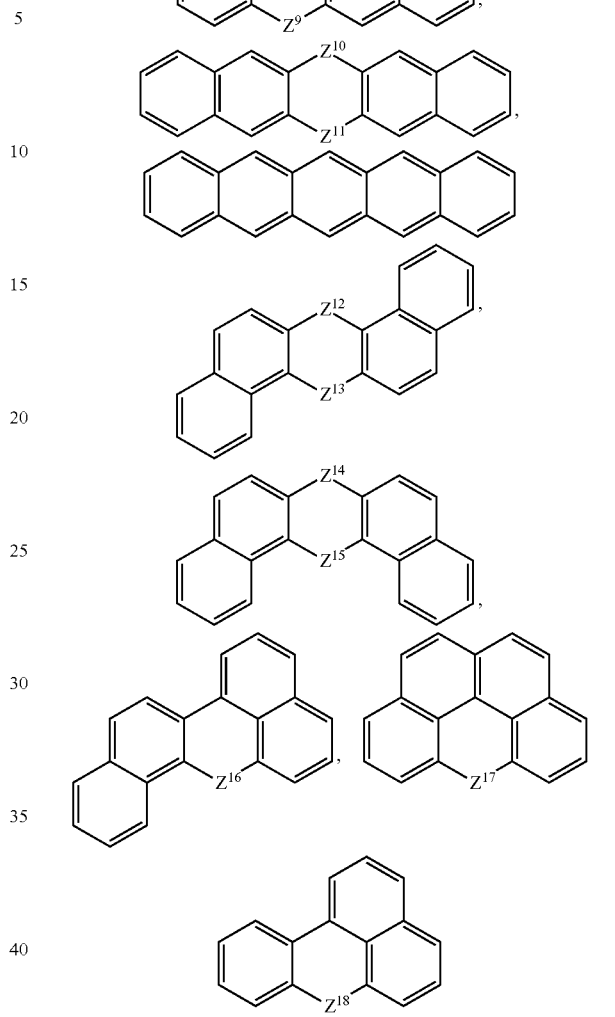

wherein, in the groups above, $Z^1$ is a single bond, a substituted or unsubstituted C1 to C20 alkylene group, a substituted or unsubstituted C3 to C20 cycloalkylene group, a substituted or unsubstituted C6 to C20 arylene group, a substituted or unsubstituted C2 to C20 heteroarylene group, a substituted or unsubstituted C2 to C20 alkenylene group, a substituted or unsubstituted C2 to C20 alkynylene group, C=O, $NR^a$, oxygen (O), sulfur (S), or a combination thereof, wherein $R^a$ is hydrogen, a substituted or unsubstituted C1 to C10 alkyl group, a substituted or unsubstituted C6 to C20 arylene group, a substituted or unsubstituted C2 to C20 heteroarylene group, a halogen atom, or a combination thereof, and $Z^3$ to $Z^{18}$ are each independently C=O, $NR^a$, sulfur (S), $CR^bR^c$, or a combination thereof, in which $R^a$ to $R^c$ are each independently hydrogen, a substituted or unsubstituted C1 to C10 alkyl group, a substituted or unsubstituted C6 to C20 arylene group, a substituted or unsubstituted C2 to C20 heteroarylene group, a halogen atom, a halogen-containing group, or a combination thereof.

11. The polymer as claimed in claim 9, wherein at least one of $X^1$ and $X^2$ is a hydroxy group.

12. The polymer as claimed in claim 11, wherein:
a is 0,
b and c are 1, and
at least one of $X^3$ and $X^4$ is a hydroxy group.

13. The polymer as claimed in claim 9, wherein:
a is 0,
b and c are 1,
at least one of $C^3$, $D^3$, and $E^3$ is a substituted or unsubstituted C1 to C30 alkyl group, a substituted or unsubstituted C6 to C30 aryl group, or a combination thereof, and
at least one of $C^4$, $D^4$, and $E^4$ is a substituted or unsubstituted C1 to C30 alkyl group, a substituted or unsubstituted C6 to C30 aryl group, or a combination thereof.

14. The polymer as claimed in claim 9, wherein the polymer has a weight average molecular weight of about 1,000 to about 200,000.

15. An organic layer composition, comprising:
a solvent; and
the monomer as claimed in claim 1.

16. The organic layer composition as claimed in claim 15, wherein the monomer is included in an amount of about 0.1 wt % to about 30 wt %, based on a total weight of the organic layer composition.

17. A method of forming patterns, the method comprising
providing a material layer on a substrate,
applying the organic layer composition as claimed in claim 15 on the material layer,
curing the organic layer composition to form a hardmask layer,
forming a silicon-containing thin layer on the hardmask layer,
forming a photoresist layer on the silicon-containing thin layer,
exposing and developing the photoresist layer to form a photoresist pattern,
selectively removing the silicon-containing thin layer and the hardmask layer and the hardmask layer using the photoresist pattern to expose a part of the material layer, and
etching an exposed part of the material layer.

18. The method as claimed in claim 17, wherein applying the organic layer composition includes performing a spin-on coating.

19. The method as claimed in claim 17, wherein the silicon-containing thin layer includes SiCN, SiOC, SiON, SiOCN, SiC, SiN, or a combination thereof.

20. The method as claimed in claim 17, further comprising forming a bottom antireflective coating prior to forming the photoresist layer.

21. An organic layer composition, comprising:
a solvent; and
the polymer as claimed in claim 9.

22. A method of forming patterns, the method comprising
providing a material layer on a substrate,
applying the organic layer composition as claimed in claim 21 on the material layer,
curing the organic layer composition to form a hardmask layer,
forming a silicon-containing thin layer on the hardmask layer,
forming a photoresist layer on the silicon-containing thin layer,
exposing and developing the photoresist layer to form a photoresist pattern,
selectively removing the silicon-containing thin layer and the hardmask layer and the hardmask layer using the photoresist pattern to expose a part of the material layer, and
etching an exposed part of the material layer.

* * * * *